United States Patent [19]

Moulin et al.

[11] B 4,001,255

[45] Jan. 4, 1977

[54] PROCESS FOR THE PRODUCTION OF CYANOPYRIDINES

[75] Inventors: Francois Moulin, Neuchatel; Karl-Josef Boosen, Erlach, both of Switzerland

[73] Assignee: Lonza, Ltd., Gampel, Switzerland

[22] Filed: Aug. 2, 1974

[21] Appl. No.: 494,339

[44] Published under the second Trial Voluntary Protest Program on March 16, 1976 as document No. B 494,339.

[30] Foreign Application Priority Data

Aug. 10, 1973 Switzerland ............... 11550/73

[52] U.S. Cl. .................................... 260/294.9
[51] Int. Cl.$^2$ ............................... C07D 213/57
[58] Field of Search ........................ 260/294.9

[56] References Cited

UNITED STATES PATENTS

| | | | |
|---|---|---|---|
| 2,839,535 | 6/1958 | Hadley et al. | 260/294.9 |
| 3,637,715 | 6/1972 | Scheidt | 260/294.9 |

*Primary Examiner*—Alan L. Rotman
*Attorney, Agent, or Firm*—Christen & Sabol

[57] ABSTRACT

The process for the production of a cyanopyridine by the conversion of a monoalkylpyridine, the alkyl having one to four carbon atoms, with (a) oxygen or air and (b) ammonia in the gaseous phase in the presence of one of several specific catalysts is known. The improvement involves the use of a catalyst which consists of pure $V_2O_5$ having a grain size of 50 to 500$\mu$ and a specific surface of up to 10 m$^2$/g and conducting the reaction at a temperature which is calculated according to the formula $T = S.m + b$, wherein T is the reaction temperature in °C., S is the specific surface of the catalyst in m$^2$/g, m is a factor of $-4$ to $-6$ and b a number from 320 to 322. Preferably the catalyst has a grain size of 100 to 250$\mu$. The molar ratio of the air to the monoalkylpyridine can be from 80:1 to 300:1, and preferably is from 150:1 to 260:1. The molar ratio of the ammonia to the monoalkylpyridine can be from 3.5:1 to 12:1, and preferably is from 4:1 to 9:1. The reaction contact time is between 0.5 and 5 seconds. The monoalkylpyridine is preferably monomethylpyridine. The reaction can, for example, be conducted in a fluidized bed. Also, any excess and/or unconverted ammonia can be recycled and used as part of the ammonia feed.

14 Claims, No Drawings

PROCESS FOR THE PRODUCTION OF CYANOPYRIDINES

BACKGROUND OF THIS INVENTION

1. Field of this Invention

This invention relates to a process for the production of cyanopyridines by reaction of monoalkyl pyridines with oxygen or air and ammonia in the gaseous phase in the presence of a catalyst, and further relates to the use of a specific catalyst which unexpectedly produces greatly improved results.

2. Prior Art

The production of cyanopyridines by reaction of alkyl substituted pyridines with ammonia and oxygen at elevated temperatures in the gaseous phase with the help of (in the presence of) catalysts.

Several different catalysts have been used in the subject reaction. For example, in U.S. Pat. No. 2,510,605 a vanadium-molybedeum-phosphorus oxide containing catalyst was used and the ammoxidation (the subject reaction) was carried out at 400°–500°C. However the yields and selectivity are bad.

According to the process of U.S. Pat. No. 2,592,123 a molybdenumoxide catalyst is used in the subject reaction at temperatures of over 410°C. Beside the disadvantages of poor yields, the catalyst also quickly loses its activity and must be frequently reactivated.

U.S. Pat. No. 2,839,535 uses a special vanadium oxide catalyst, which is applied to pre-treated $Al_2O_3$. The patent teaches that it is of the utmost importance that the $Al_2O_3$ be pretreated at temperatures of 1,150° to 1,400°C., otherwise poor yields are obtained. Beside this disadvantage, the catalyst becomes inactive in the course of time during the reaction and must be regenerated.

According to U.S. Pat. No. 3,297,587 the ammoxidation must be carried out with the use of borophosphate catalysts activated with compounds of the metals bismuth, molybdenum, vanadium, iron or cobalt. This process too was not satisfactory since these catalysts are partly split into boric acid and phosphoric acid during the reaction.

German (published) application No. 1,770,841 uses tin-phosphate catalysts activated with molybdenum, bismuth, vanadium, iron or cobalt. Disadvantages of the process of the German Application publication consists of, on the one hand in fact, that these special catalysts must first be produced, and, on the other hand in the fact that, as temperatures of 300° to 700°C. are used, the phenomena of decomposition has already occurred.

BROAD DESCRIPTION OF THIS INVENTION

The process for the production of a cyanopyridine by the conversion of a monoalkylpyriddine, the alkyl having one to four carbon atoms, with (a) oxygen or air and (b) ammonia in the gaseous phase in the presence of one of several specific catalysts is known.

This invention involves the improvement in such process (the subject process) of using a catalyst which consists of pure $V_2O_5$ having a grain size of 50 to 500 $\mu$ and a specific surface of up to 10 $m^2/g$ and conducting the reaction at a temperature which is calculated according to the formula $T = S.m + b$, wherein T is the reaction temperature in °C., S is the specific surface of the catalyst in $m^2/g$, m is a factor of −4 to −6 and b a number from 320 to 322.

The catalyst preferably has a grain size of 100 to 250 $\mu$. The molar ratio of the air to the monoalkylpyridine can be from 80:1 to 300:1, and preferably is from 150:1 to 260:1. The molar ratio of the ammonia to the monoalkylpyridine can be from 3.5:1 to 12:1, and preferably is from 4:1 to 9:1. The reaction contact time is between 0.5 and 5 seconds. The reaction, for example, can be conducted in a fluidized bed. Also, any excess and/or unconverted ammonia is recycled and used as part of the ammonia feed. The monoalkylpyridine is preferably a monomethylpyridine.

The use of $V_2O_5$ (by itself) as the catalyst in the subject reaction is not known. The $V_2O_5$ catalyst is quite different from the catalysts known to have been used in the subject reaction and unexpectedly produces greatly improved results.

The use of $V_2O_5$ (by itself) as a catalyst in the subject reaction allows the use of a reaction temperature which is generally lower than that used when previously used catalysts are used.

The use of $V_2O_5$ (by itself) in the subject reaction results in higher yields and selectivity than compared to previously used catalysts. The $V_2O_5$ catalyst has relatively long-term activity, thus avoiding the disadvantage of having to be frequently reactivated. The $V_2O_5$ catalyst does not have to be specially pre-treated or does not have any carrier or other active ingredient which must be specially pre-treated. The $V_2O_5$ catalyst is not decomposed during the subject reaction. The $V_2O_5$ catalyst regenerates itself under the reaction conditions of this invention and suffers no deactivation whatsoever.

The (mono) cyanopyridines produced by this invention are valuable starting materials for the synthesis or production of 2-pyridine carboxylic acid or iso-nicotinic acid derivatives, which are used as pharmaceutical products and as additives to cattle fodder.

DETAILED DESCRIPTION OF THIS INVENTION

The monoalkylpyridines (i.e., having one alkyl group) are useful. The alkyl group can be one to four carbon atoms. Preferably the monoalkylpyridine is a monomethylpyridine. Examples of useful alkylpyridines are 2-methyl-pyridine ($\alpha$-picoline), 3-methyl-pyridine ($\beta$-picoline), 4-methyl-pyridine ($\gamma$-picoline), 2-ethyl-pyridine, 2-isopropyl-pyridine, 3-ethyl-pyridine, 4-isopropyl-pyridine, 4-ethyl-pyridine, 2-propyl-pyridine, 2-butyl-pyridine, 4-propyl-pyridine, 4-butyl-pyridine, 2-isobutyl-pyridine, 2-tert.butyl-pyridine and 4-isobutyl-pyridine.

The $V_2O_5$ catalyst, which is useful in the process of this invention, is commercially obtainable and requires no further pretreatment. The $V_2O_5$ catalyst can also be produced, for example, by thermal treatment of $NH_4VO_3$ in an oxygen atmosphere. The $V_2O_5$ catalyst of this invention does not incorporate any other ingredients or utilize a carrier. One of several advantages of the $V_2O_5$ catalyst is that it regenerates itself under the reaction conditions, therefore suffers no deactivation whatsoever.

The conversion, according to this invention, of alkyl pyridine with ammonia and molecular oxygen into cyanopyridine is carried out effectively in a fluidized bed. (The catalyst can also be disposed fixedly in the reaction space; for this purpose, however, the reaction conditions must be adapted to such circumstances.)

The catalyst already has its full activity at the beginning of the operating time (reaction) and such activity is maintained unchanged throughout the reaction. No reactivation of the catalyst is required.

The oxygen needed for the conversion of the alkyl pyridine with ammonia into cyanopyridine can be fed in a pure state or in the form of air. The molar ratio of air to alkyl pyridine can vary between 80:1 and 300:1 and more effectively between 100:1 and 280:1. Preferably the molar ratio of air to alkyl pyridine is between 150:1 to 260:1. The molar ratio of oxygen to alkyl pyridine, when oxygen is used in place of air, is calculated on a proportion of the percentage of oxygen in air.

The molar ratio of ammonia to alkyl pyridine 3.5:1 and 12:1 and preferably is between 4:1 and 9:1. The excess ammonia that is used and the unconverted ammonia can be kept in circulation and again fed into (recycled into) the reaction rate. The loss of ammonia is exceedingly small — as the reaction temperatures used are so low, practically no oxidation of the ammonia takes place.

During the execution of the process of this invention, the contact times are between 0.5 and 5 seconds, and more effectively are between 1.0 and 2.0 seconds. The contact time is defined as the time which is required theoretically by a molecule of the reaction gas to pass through the layer of catalyst.

The cyanopyridines produced according to this invention are valuable starting substances for the synthesis of 2-pyridine carboxylic acid or iso-nicotinic acid derivatives, which are used as pharmaceutical products and as additives to cattle fodder.

Since the ammoxidation of alkylpyridines is strongly exothermal, the energy obtained from the invention process can be effectively utilized, for example, for the production of steam. This energy, according to the invention process, can be fully utilized as the process of this invention does not have to be carried out in the presence of steam.

The following examples illustrate this invention. As used herein, all percentages, parts, ratios and the like are on a weight basis, unless otherwise stated or otherwise obvious to one ordinarily skilled in the art.

EXAMPLE 1

75 cm$^3$ of a V$_2$O$_5$ powder having a 99.6 percent purity, 6 m$^2$/g specific surface and a grain size of 100 to 250 $\mu$ were heated in a fluidized bed reactor (having a cross section 17 cm$^2$ and a length of 40 cm) to 291°C. Then a stream of gas, consisting of 2.9 ml/hr. of $\beta$-picoline (30 ml mole), 5.25 l/hr. of NH$_3$ and 180 l/hr of air, which had been previously passed through a tube furnace heated to about 300°C., was introduced into the reactor. Under these conditions, the contact time amounted to 1.35 second. Then the reaction gases were cooled to ambient temperature and absorbed in methanol at −10°C., whereby nicotinic acid, unconverted $\beta$-picoline and small quantities of NH$_3$ were dissolved. This absorption method is required whenever exact analyses of a passage are desired in laboratory experiments. After 2 hours of reaction time, a content of 0.6 g of $\beta$-picoline and 5.21 g of nicotinic acid (NS)-nitrile were found in 456 ml. of methanol by gas chromatographic analysis. This corresponded to a yield of 83.5 percent of theory of nicotinic acid nitrile. The unconverted 10.7 percent of $\beta$-picoline could be recovered without difficulty. The yield, related to converted $\beta$-picoline (selectivity) thus amounted to 93.5 percent of theory.

The results listed in Table 1 were obtained using similar reaction conditions.

TABLE 1

| Temperature, °C | Yield in % Related to $\beta$-picoline used | Recaptured $\beta$-picoline in % | Selectivity, % |
|---|---|---|---|
| 275* | 60.1 | 34.0 | 91.1 |
| 280 | 74.0 | 20.4 | 93.0 |
| 286 | 76.8 | 12.2 | 87.5 |
| 291 | 84.3 | 6.6 | 90.2 |
| 291 | 82.0 | 10.2 | 92.1 |
| 291 | 83.5 | 10.7 | 93.5 |
| 297 | 81.9 | 2.5 | 83.7 |
| 297 | 81.9 | 4.1 | 85.5 |
| 302* | 76.8 | 5.0 | 80.8 |
| 308* | 75.8 | 0 | 75.8 |
| 325* | 73.8 | 0 | 73.8 |
| 341* | 69.7 | 0 | 69.7 |
| 357* | 65.5 | 0 | 65.5 |

Table 1 shows that in the case of the yields designated by an asterik (not according to this invention) worse yields resulted and that they showed a lesser selectivity.

EXAMPLE 2

Proceeding as in Example, 1 but changing the catalyst, the catalyst was heated to a temperature of 320°C. The catalyst consisted of a V$_2$O$_5$ powder having a purity of 99.6 percent, an average grain size of 100 to 250 $\mu$, and a specific surface of 0.1 m$^2$/g. The reaction was conducted as in Example 1. The yield amounted to 85.0 percent of theory of nicotinic acid nitrile and the quantity of unconverted $\beta$-picoline amounted to 9.0 percent. The selectivity amounted to 93 percent of theory.

The results listed in Table 2 where achieved under similar reaction conditions.

TABLE 2

| Temperature, °C | Yield in % related to $\beta$-picoline used | Recaptured $\beta$-picoline in % | Selectivity, % |
|---|---|---|---|
| 300 | 63.1 | 26.3 | 85.5 |
| 320 | 85.0 | 9.0 | 93.0 |
| 320 | 81.5 | 10.0 | 91.0 |
| 320 | 76.2 | 23.3 | 99.0 |
| 320 | 84.9 | 12.9 | 97.5 |
| 320 | 82.7 | 13.1 | 95.0 |
| 320 | 76.0 | 22.0 | 97.5 |
| 320 | 82.0 | 7.9 | 89.0 |
| 335 | 72.9 | 4.0 | 76.0 |

The first and last experiments from Table 2 were outside the claimed range and had poor yields and selectivities.

EXAMPLE 3

Example 1 was repeated, but $\gamma$-picoline was used as the starting material. 75 cm$^3$ of a V$_2$O$_5$ powder having a 99.6 percent purity, a 6 m$^2$/g specific surface and a grain size of 100–250 $\mu$, was heated at 284°C. Then a stream of gas, consisting of 2.9 ml.hr of $\gamma$-picoline (29.8 mMol/hr), 5.25 l/hr of NH$_3$ and 180 l/hr of air, which previously had then passed through a tube furnace heated to about 300°C., was introduced into the reactor. Under these conditions the contact time amounted to 1.35 second. After that the reaction gases were colled to ambient temperature and absorbed in methanol at −10°C, whereby isonicotinic acid nitrile, unconverted γ-picoline and small quantities of $NH_3$ were dissolved. After 2 hours of reaction time, a content of 0.09 gm of γ-picoline and 5.02 g of isonicotinic acid nitrile were found in 485 ml of methanol by gas chromatographic analysis. This corresponded to a yield of 81.2 percent theory of isonicotinic acid nitrile. There was 1.6 percent of γ-picoline which was not converted. The yield, related to converted γ-picoline, (selectivity) amounted to 82.7 percent. The additional results, listed in Table 3, where achieved under similar reaction conditions.

TABLE 3

| Temperature, °C | Yield % | γ-picoline recaptured % | Selectivity, % |
|---|---|---|---|
| 284 | 81.2 | 1.6 | 82.7 (Example 3) |
| 291 | 81.3 | 0.6 | 81.7 |
| 298 | 81.7 | 0.7 | 82.3 |

EXAMPLE 4

Example 1 was repeated however the reaction was accomplished with α-picoline. 125 ml of a $V_2O_5$ powder having a 99.6 percent purity, a 6 m²/g specific surface and a grain size of 100 to 250 μ were used. The catalyst was heated to 291°C and a gas stream, consisting of 2.9 ml/hr of α-picoline (29.6 m mole/hr), 5.25 l/hr of $NH_3$ and 180 l/hr of air, which had previously passed through a tube furnace heated to about 300°C, was introduced into the reactor. The contact time amounted to 1.70 second. The end products were absorbed, and 2.04 g of α-picoline and 2.71 g of picoline nitrile were found in 483 ml of methanol after 2 hours of reaction time by gas chromatographic analysis. This corresponded to a yield of 44.2 percent picoline nitrile. 37.3 percent of α-picoline were not converted. The yield, related to converted α-picoline, (selectivity) amounted to 70.5 percent.

Table 4 shows the results of Examples 1 and 2 (according to this invention) compared with the results of Examples 5 to 7 (not according to this invention). The results shows a clear progression of dimiminshing results (and show the inventiveness of this invention).

TABLE 4

| Example No. | Temperature °C | Catalyst | yield (%) related to the amount of α-,β-orγ-picoline used | Loss, % | Selectivity, % |
|---|---|---|---|---|---|
| 1 | 291 | $V_2O_5$ 6 m²/g | 83.5 | 5.8 | 93.5 |
| 2 | 320 | $V_2O_5 \cong 0.1$ m²/g | 85.0 | 6.0 | 93.0 |
| 5 | 320 | 1.4% $V_2O_5/TiO_2$ | 68.6 | 17.1 | 80.0 |
| 6 | 340 | 5.6% $V_2O_5/Al_2O_3$ | 72.1 | 21.9 | 76.9 |
| 7 | 515 | $MoO_2$ + 5% $V_2O_5$ on tin phosphate | 72.5 | ? | 78.0 |

What is claimed is:

1. In a process for the production of a cyanopyridine by conversion of a monoalkylpyridine, the alkyl having one to four carbon atoms, with (a) oxygen or air and (b) ammonia in the gaseous phase in the presence of a catalyst, the improvement which consisting essentially of using a catalyst which consists of pure $V_2O_5$ having a grain size of 50 to 500 μ and a specific surface of up to 10 m²/g and conducting the reaction at a temperature which is calculated according to the formula T = S.m + b, wherein T is the reaction temperature in °C., S is the specific surface of the catalyst in m²/g, m is a factor of −4 to −6 and b a number from 320 to 322.

2. A process as described in claim 1 wherein the catalyst has a grain size of 100 to 250 μ.

3. A process as described in claim 1 wherein the molar ratio of the air to the monoalkylpyridine is from 80:1 to 300:1.

4. A process as described in claim 1 wherein the molar ratio of the air to the monoalkylpyridine is from 150:1 to 260:1.

5. A process as described in claim 1 wherein the molar ratio of the ammonia to the monoalkylpyridine is from 3.5:1 to 12:1.

6. A process as described in claim 1 wherein the molar ratio of the ammonia to the monoalkylpyridine is from 4:1 to 9:1.

7. A process as described in claim 1 wherein the reaction contact time is between 0.5 and 5 seconds.

8. A process as described in claim 1 wherein the monoalkylpyridine is a monomethylpyridine.

9. A process as described in claim 8 wherein the monomethylpyridine is β-picoline.

10. A process as described in claim 1 wherein the reaction is conducted in a fluidized bed.

11. A process as described in claim 1 wherein any excess and/or unconverted ammonia is recycled and used as part of the ammonia feed.

12. A process as described in claim 1 wherein the catalyst has a grain size of 100 to 250 μ, the molar ratio of the air to the monalkylpyridine is from 80:1 to 300:1, the molar ratio of the ammonia to the monalkypyridine is from 3.5:1 to 12:1, and the reaction contact time is between 0.5 and 5 seconds.

13. A process as described in claim 12 wherein the reaction is cuoducted in a fluidized bed.

14. A process as described in claim 13 wherein any excess and/or unconverted ammonia is recycled and used as part of the ammonia feed.

* * * * *